United States Patent [19]

Hashim

[11] 4,113,858
[45] Sep. 12, 1978

[54] NOVEL COMPOUNDS, COMPOSITIONS AND METHODS OF THEIR USE

[75] Inventor: George A. Hashim, Irvington, N.Y.

[73] Assignee: St. Luke's Hospital, New York, N.Y.

[21] Appl. No.: 648,379

[22] Filed: Jan. 12, 1976

Related U.S. Application Data

[63] Continuation-in-part of Ser. No. 542,175, Jan. 20, 1975, abandoned, which is a continuation-in-part of Ser. No. 315,140, Dec. 12, 1972, Pat. No. 3,864,481.

[51] Int. Cl.$^2$ .................... A61K 37/00; C07C 103/52
[52] U.S. Cl. ............................. 424/177; 260/112.5 R
[58] Field of Search .................. 260/112.5 R; 424/177

[56] References Cited

U.S. PATENT DOCUMENTS

| | | | |
|---|---|---|---|
| 3,247,180 | 4/1966 | Schwyzer et al. | 260/112.5 R |
| 3,864,481 | 2/1975 | Hashim | 424/177 |
| 3,941,162 | 3/1976 | McCabe et al. | 260/112.5 R |

FOREIGN PATENT DOCUMENTS

| | | | |
|---|---|---|---|
| 84,475 | 5/1962 | France | 260/112.5 R |
| 85,518 | 5/1962 | France | 260/112.5 R |
| 88,104 | 5/1962 | France | 260/112.5 R |
| 88,722 | 5/1962 | France | 260/112.5 R |
| 1,310,534 | 10/1962 | France | 260/112.5 R |
| 1,336,686 | 7/1963 | France | 260/112.5 R |

OTHER PUBLICATIONS

E. H. Eylar, et al., J. Biol. Chem., 246, No. 18, (1971), pp. 5770–5784.

Primary Examiner—Delbert R. Phillips
Attorney, Agent, or Firm—Kane, Daisimer, Kane, Sullivan and Kurucz

[57] ABSTRACT

Synthetic compounds of the formula:

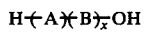

are disclosed wherein X is an integer of at least 0 and A and B each represent a divalent moiety of the formula:

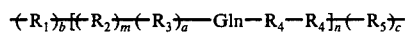

wherein $R_1$ and $R_5$ are each selected from the residue of an amino acid or a polypeptide; $R_2$ represents the residue of tryptophan or tyrosine; $R_3$ represents the residue of an amino acid; $R_4$ represents the residue of lysine; arginine or histidine; $a$ is an integer of 0 to 4, inclusive; $b$ and $c$ are each integers of at least 0; $m$ is an integer of from 0 to 1, inclusive; and $n$ is an integer of at least 1; provided that when $R_1$ or $R_5$ is the residue of a polypeptide, the corresponding $b$ or $c$ is 1.

The disclosure is also of intermediate compounds for preparing the compounds of the above formula and derivative compounds having biological activity.

Disclosed also are pharmaceutical compositions wherein the essential active ingredient is a synthetic compound of the invention and methods of using them for the prevention, suppression, treatment and diagnosis of multiple sclerosis.

15 Claims, No Drawings

NOVEL COMPOUNDS, COMPOSITIONS AND METHODS OF THEIR USE

CROSS-REFERENCE TO RELATED APPLICATIONS

This application is a continuation-in-part of copending application Ser. No. 542,175 filed Jan. 20, 1975 now abandoned and, which in turn is a continuation-in-part of application Ser. No. 315,140 filed Dec. 12, 1972 and now U.S. Pat. No. 3,864,481.

BACKGROUND OF THE INVENTION

1. Field of the Invention

The invention concerns novel synthetic polypeptides and their use in the diagnosis and treatment of multiple sclerosis; intermediates and derivatives thereof.

2. Brief Description of the Prior Art

It has been reported that the basic protein isolated from myelin of the central nervous system of man and animals induces experimental allergic encephalomyelitis (EAE), an auto-immune disease of the central nervous system. The structure for the basic protein was published by E. H. Eylar, Steven Brostoff, George Hashim, Juanita Caccam, and Paul Burnett entitled "Basic A1 Protein of the Myelin Membrane", The Journal of Biological Chemistry, Vol. 246, No. 18, Issue of Sept. 25, 1971, pp. 5770–5784. Also, it has been shown that the disease inducing basic protein is readily hydrolyzed by proteolytic enzymes. It is also known that there is more than one disease inducing region found on the native basic protein molecule. These regions have been isolated in the form of peptides following hydrolysis of the basic protein. The essential requirement for disease induction in the guinea pig is the linear sequence of at least nine amino acid residues having the schematic of formula:

H-Phe-Ser-Trp-Gly-Ala-Glu-Gly-Gln-Lys-OH

For convenience, the amino acid groups in the above formula, and at times hereinafter, are referred to by abbreviations, following accepted and common practice in peptide chemistry. For example, the following abbreviations for amino acids are used, at times, throughout the following specification and claims:

Lys - lysine
His - histidine
Arg - arginine
Thr - threonine
Ser - serine
Glu - glutamic acid
Pro - proline
Gln - glutamine
Gly - glycine
Ala - alanine
Leu - leucine
Ileu - isoleucine
Tyr - tyrosine
Trp - tryptophan
Phe - phenylalanine In each instance herein, it should be understood that in referring to amino acids, both the D- and L-isomeric forms are intended to be identified unless otherwise indicated.

For disease induction of guinea pigs the linear sequence of amino acid residues required is of the schematic formula:

H-Phe-Ser-Trp-Gly-Ala-Glu-Gly-Gln-Arg-OH and for disease induction in monkeys and rabbits the linear sequence of amino acid residues required is of the schematic formula:

H-Thr-Thr-His-Tyr-Gly-Ser-Leu-Pro-Gln-Lys-OH.

Investigators have shown that EAE can be induced in animals by administering a natural compound having one of the disease inducing regions of the basic proteins. Other disease inducting peptides produced from the native basic protein by hydrolysis have been isolated. The disease induced by the active regions has the same clinical and pathological manifestations as that produced when the whole protein is administered.

Unexpectedly, the administration to a mammal of the synthetic compounds of my invention does not induce disease in the mammals as occurs upon administration of the naturally occurring analogs.

SUMMARY OF THE INVENTION

The invention comprises synthetic compounds of the formula:

  (I)

and the acid addition salts thereof,
wherein X is an integer of at least O; A and B each represent a divalent moiety of the formula:

  (II)

wherein $R_1$ and $R_5$ are each selected from the residue of an amino acid and the residue of a polypeptide; $R_2$ is selected from the residue of tryptophan and tyrosine; $R_3$ represents the residue of an amino acid; $R_4$ is selected from residue of lysine, arginine and histidine; a is an integer of from 0 to 4, inclusive; b and c are each integers of at least 0; m is an integer of from 0 to 1, inclusive; and n is an integer of at least 1; provided that when $R_1$ is the residue of a polypeptide, b is 1 and when $R_5$ is the residue of a polypeptide, c is 1.

Although theoretically there is no upper limit to the integer value of x, b, c and n, except as hereinbefore provided for, as a practical matter their upper values are limited by the preference that the molecular weight of the compound (I) be less than about 100,000.

Within the scope of the formula (I) given above are compounds of the formulae:

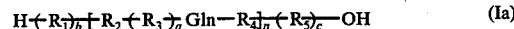  (Ia)
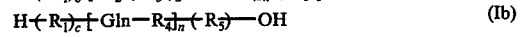  (Ib)

wherein $R_1$, $R_2$, $R_3$, $R_4$, $R_5$, a, b, c and n are as previously defined and

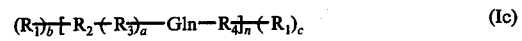  (Ic)

wherein $R_1$, $R_2$, $R_3$, $R_4$, $R_5$, a, b, c and n are as previously defined, provided further $R_1$ is a polypeptide having at least a single amino acid residue.

The invention also comprises a pharmaceutical composition, which comprises; an effective amount for the prevention, suppression, treatment and diagnosis of multiple sclerosis of a compound of the formula (I) above, in admixture with a pharmaceutically acceptable parenteral carrier. Such pharmaceutical compositions include parenterally administrable therapeutic unit dosage forms which comprise from about 0.005 mg to about 1,000 mg. of a synthetic compound of the formula (I) in a milliliter of a pharmaceutically acceptable parenteral carrier.

The invention also comprises a method of treating a mammal which is useful for the prevention, suppression and diagnosis of multiple sclerosis, which comprises; administering to said mammal from about 0.0001 to about 25 mg. per kologram of body weight of a snythetic compound of the formula:

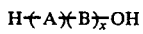

wherein A, B and X are as previously defined; provided that when X is O then A is the divalent moiety of the formula (II) above, wherein at least one of $R_1$ and $R_5$ is specifically the residue of a polypeptide.

The synthetic compounds (I) of the invention are useful for inhibiting the induction of experimental allergic encephalomyelitis (EAE). Experimental allergic encephalomyelitis is the experimental model disease for multiple sclerosis in humans. The synthetic compounds (I) of the invention are non-encephalitogenic when administered in therapeutic dosages to mammals and are useful for the prevention, suppression, treatment and diagnosis of multiple sclerosis in mammals including humans. The administration of therapeutic dosage units of the synthetic compounds (I) will prevent the reoccurrence of encephalomyelitis and suppress in the active stage further deterioration of nervous tissue in mammals including human beings. Such administration to mammals will also prevent the formation of newly sennsitized cells and block active sensitized cells from doing damage to nervous tissue.

The term "synthetic compound" is used throughout the specification and claims in its normally accepted sense as meaning a man-made product of chemical synthesis, as opposed to products of nature.

The term "residue of an amino acid" is used herein to mean the divalent moiety obtained upon the removal of the hydroxyl of a carboxyl group and the hydrogen atom from the amino group of an amino acid. Illustrative of such is a divalent moiety of formula:

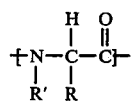

wherein R, when taken independently, represents hydrocarbyl or hydrocarbyl substituted with an inert group; R' when taken independently is hydrogen; and R and R' when taken together represent the divalent moiety of formula:

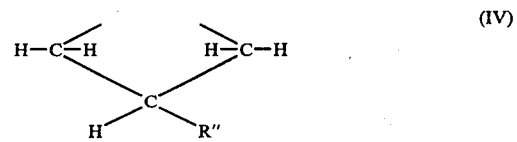

wherein R" represents hydrogen or hydroxyl.

The term "hydrocarbyl" as used throughout the specification and claims means that monovalent moiety obtained upon removal of a hydrogen atom from a parent hydrocarbon. Illustrative of hydrocarbyl are alkyl groups such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and isomeric forms thereof; cycloalkyl groups such as cyclopropyl, cyclobutyl, cyclopentyl, cyclohexyl, cycloheptyl, cyclooctyl, 2-methylcyclopentyl, 2,3-dimethylcyclobutyl, 4-methylcyclobutyl, 3-cyclopentylpropyl and the like; cycloalkenyl groups such as cyclobutenyl, cyclopentenyl, cyclohexenyl, cycloheptenyl, cyclooctenyl and the like, including isomeric forms thereof; cycloalkadienyl groups such as cyclopentadienyl, cyclohexadienyl, cycloheptadienyl and the like; aryl groups such as phenyl, tolyl, xylyl, naphthyl, biphenylyl and the like; aralkyl groups such as benzyl, phenethyl, phenpropyl, naphthmethyl and the like.

The term "hydrocarbyl substituted with an inert group" as used herein means a hydrocarbyl group as defined above wherein one or more hydrogen atoms have been replaced with a group such as hydroxyl, carboxyl, amino, guanidino, mercapto, methylthio,

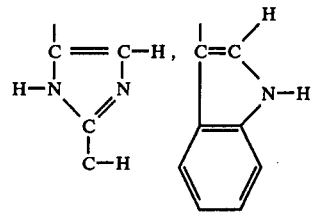

and like groups.

The term "residue of a polypeptide" means the monovalent moiety obtained upon the removal of a hydrogen atom or a hydroxyl group from a polypeptide having within its structural makeup a terminal amino acid group, including di-, tri-, and higher polypeptides.

The term "polypeptide" as used herein includes a protein, recognizing that the latter are by convention generally considered to be polypeptides having a molecular weight over about 10,000 and of a more complex nature being made up of polypeptide chains.

DETAILEED DESCRIPTION OF THE INVENTION

The Compounds of the Invention

The compounds (I) of the invention may be prepared according to conventional and well-known methods of synthesizing polypeptides. Illustrative of those methods which may be employed are the solid phase peptide synthesis procedures described by R. B. Merrifield in the Journal of the American Chemical Society, Vol. 85, p. 2149 (1963); by G. R. Marshall and R. B. Merrifield, Biochhemistry, Vol. 4, p. 2394, (1965); and by A. Marglin and R. B. Merrifield, Journal of the American Chemical Society, Vol. 88, p. 5051 (1966). In general, the method comprises starting with the first amino acid desired in the sequence, linked as an ester to a benzyl group on an insoluble polymer such as polystyrene. The alpha-amino group is condensed with a second amino-protected and activated amino acid followed by deblocking so that the peptide grows on the polymer support.

The resin (polymer support + peptide), in tiny granules, is simply steeped in excess amino acid derivative, then washed, then treated with acid and washed again and the sequence repeated with desired amino acids until the desired amino acid additions and sequences are obtained. Then the resin is treated with stronger acid to remove peptide from the polymer benzyl groups (via $S_N1$ solvolsis at benzyl carbons). Generally, the entire procedure is carried out under an inert atmosphere (nitrogen) and at room temperatures. Completion of each sequence in the overall procedure is readily observed by conventional techniques, i.e.; infrared analysis, thin-layer chromatography and like methods of analysis.

The peptides so prepared generally are recovered in pure forms by conventional techniques such as filtration, recrystallization, counter-current distribution, chromatography and like methods. For complete details of the solid-phase method of peptide synthesis, see Merrifield, supra.

The relatively high molecular weight compounds (I) of the invention, i.e.; those wherein $R_1$ and/or $R_5$ are residues of a polypeptide may also be conveniently prepared by condensing the corresponding compound of formula:

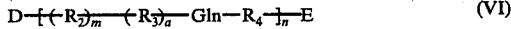

$$D-[(-R_2)_m-(-R_3)_a-Gln-R_4-]_n-E \qquad (VI)$$

wherein $R_2$, $R_3$, $R_4$, $a$, $m$ and $n$ are as defined above; one of D and E is hydroxyl and the other of D and E is hydrogen; with a polypeptide, including a natural polypeptide such as albumin or gamma globulin. The reaction may be carried out according to the method of Merrifield, supra. The starting compounds (VI) may also be prepared following the procedure of Merrifield, supra.

Those compounds of the formula (I) wherein $n$ is greater than 1 or where X is greater than 0 are conveniently prepared by condensation of the approximate and corresponding compounds (VI) either sequentially or randomly as desired. The method is well known; see for example Hirshmann et al., JACS, 91,507, (1969). Alternatively, such compounds within the scope of the formula (I) may be prepared by the random polymerization of the appropriate N-carboxy anhydrides of the corresponding component peptides and amino acids; see for example the methods described in Lorenzi, et al., Biochem., 10, 3046, (1971) and Friedman, et al., JACS, 83, 4050, (1961).

The alpha-amino acids employed to prepare the compounds (I) of the invention are of the general formula:

$$\begin{array}{c} \text{H} \quad \text{O} \\ | \quad \| \\ \text{H—N—C—C—OH} \\ | \quad | \\ \text{R}' \quad \text{R} \end{array} \qquad (VII)$$

wherein R and R' are as previously defined. The amino acids of formula (VII) are a well-known class of compounds prepared by a variety of well-known procedures; for example, by reduction of α-oximino acids (Barry et al., J. Org. Chem., 12, 460 (1947); by hydrolysis of hydantoins (Ware, Chem. Revs. 46, 403, (1950); by reaction of α-halo acids with ammonia (Marvel, Org. Syn., Vol. 20, pg. 106; Vol. 21, pgs. 60 and 74); reductive amination of α-keto acids [Knoop et al., Z. physiol. Chem., 148, 294 (1925) and 170, 186 (1927)]; and from α-amino cyanides by the well-known Strecker synthesis (Allen et al., Org. Syn., Coll. Vol. 3, 275). A review of various α-amino acids and methods of synthesis can be found in the text "Chemistry of the Amino Acids", supra., Chapter 8.

Representative of preferred α-aminoacids employed in preparing preferred compounds (I) are the naturally occurring amino acids such as lysine, histidine, arginine, threonine, serine, glutamic acid, proline, glutamine, glycine, alanine, leucine, isoleucine, tyrosine, tryptophan and phenylalanine. Both the D- and L-stereoisomer forms may be used with a preference for the L-form.

The invention relates also to pharmaceutical dosage unit forms of systemic (parenteral) administration, which are useful for the diagnosis, suppression or prevention of multiple sclerosis in mammals. The term "dosage unit form" as used in this specification and in the claims refers to physically discrete units suitable as unitary dosages for mammalian subjects, each unit containing a predetermined quantity of the essential active ingredient, i.e.; a compound (I), calculated to produce the desired effect in combination with the required pharmaceutical means which adapt said ingredient for systemic administration. Examples of dosage unit forms in accordance with this invention are sterile preparations in liquid vehicles for parenteral administration and sterile dry preparations for the extemporaneous preparation of sterile injectable preparations in a liquid vehicle. Carriers or vehicles include vegetable oils, water, ethanol, and polyols, for example, glycerol, propylene glycol, liquid polyethylene glycol, and the like. Liquid pharmaceutical preparations for parenteral administration prepared in water or aqueous solutions advantageously contain suspending agents, such as for example, sodium carboxymethylcellulose and the like. They must be sterile and must be fluid to the extent that easy syringeability exists. Parenteral preparations must also be stable under the conditions of manufacture and storage, and ordinarily contain in addition to the basic solvent or suspending liquid, preservatives in the nature of bactericidal and fungicidal agents, for example, parabens, chlorobutanol, benzyl alcohol, phenol, thimerosal, and the like. In many cases it is preferable to include isotonic agents, for example, sugars or sodium chloride. Any solid preparations for subsequent extemporaneous preparation of sterile injectable preparations are sterilized, preferably by exposure to a sterilizing gas, such as for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.001 mg. to about 1000 mg. of the essential active ingredient [a compound of formula (I)] per dosage unit form. The amount of the essential active ingredient provided in the pharmaceutical dosage unit forms is based on my finding that the effective amount of compounds (I) of the invention, for obtaining the desired therapeutic effect in mammals is within a range from about 0.001 mg. per kg. to about 25 mg. per kg. of body weight of the recipient, daily. Preferably 0.5 mg./kg. to about 5 mg./kg. daily is provided. The preferred amount for diagnosis of multipl sclerosis is within the range of from about 0.0001 mg. to about 1.0 mg. per kg. of body weight of the recipient mammal.

Use For Diagnosis of Multiple Sclerosis in Mammals

Any compound of the formula (I) above may be used to obtain a positive diagnosis of multiple sclerosis in mammals. The procedure comprises, advantageously, the sub-cutaneous administration to the mammal of at least one microgram of a compound (I) in an acceptable pharmaceutical carrier. A delayed type of skin hypersensitivity reaction elicited in response to the administration is a positive indication for the diagnosis of multiple sclerosis. The extent of the positive reaction may be measured and reported in mm diameter of the erythema formed. A reaction is considered positive when the erythema is visible after 3–6 hours and reaches maximum size at 24 hours.

For the diagnosis of multiple sclerosis, those compounds within the scope of formula (I) having the more specific formula:

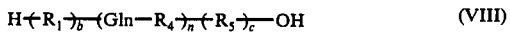

$$H\!-\!(R_1)_b\!-\!(Gln\!-\!R_4)_n\!-\!(R_5)_c\!-\!OH \qquad (VIII)$$

wherein $R_1$, $R_4$, $R_5$, $b$, $c$ and $n$ are as previously defined are preferred. Most preferred are those wherein $R_1$ is the residue of tyrosine or tryptophan. Any enlargement of the molecular weight of the polypeptide of the formula (VIII) by addition of a polypeptide such as albumin or gamma globulin or the like at the C-terminal amino acid residue or the N-terminal amino residue will enhance the delayed type skin response and reduce the dosage required for diagnosis. Such macromolecular compounds (VIII) are particularly preferred. Also preferred compounds (I) for the diagnosis of multiple sclerosis in mammals are those wherein $n$ is at least 4.

Therapeutic Use

The compounds (I) of the invention may be administered to mammals in therapeutic dosages which vary over a broad range. A therapeutic dose for treatment of mammals may be at least one microgram (0.001 mg) per kilogram body weight and may include about 25 mg. per kilogram body weight. Generally, the amount administered per kilogram of body weight may be reduced as a function of molecular weight. The preferred therapeutic dose generally varies from 0.5 mg to 5.0 mg per kilogram of body weight.

Procedure for Administration to Mammals

A. For prevention of multiple sclerosis in mammals the compounds (I) of the invention may be administered subcutaneously or intramuscularly in association with a pharmaceutically acceptable parenteral carrier.

B. For the treatment of multiple sclerosis in mammals the compounds (I) of the invention may be administered intramuscularly, subcutaneously or intravenously or in any combination thereof.

The following examples describe the manner and process of making and using the invention and set forth the best mode contemplated by the inventor of carrying out the invention, but are not to be construed as limiting.

PREPARATION 1

The blocked or t-butyloxycarbonyl amino acids (referred to hereinafter for convenience as t-Boc amino acid) used in the preparation of the compounds (I) of the invention may be purchased commercially or they may be prepared according to the method of Schwyzer et al., Helv. Chem. Acts., 42, 2622, (1959). Similarly, the t-Boc- amino acids - resin esters are available commercially or they may be prepared according to the procedure of Merrifield, supra.

EXAMPLE 1

(A)

A suitable reaction vessel is charged with 2.0 gms. of cross linked poly-vinyl chloride resin containing from 0.25 to 0.5 moles of L-glycine per gram (Boc-L-glycine-resin ester, Peninsula Laboratories, Inc., San Carlos, CA). The vessel is then vented and repeatedly pressured with nitrogen gas to remove all traces of air from the reaction vessel. The vent is then closed to maintain a nitrogen gas atmosphere in the reaction vessel.

(B) Deblocking the Starting Boc-L-glycine Resin Ester

While maintaining the nitrogen gas atmosphere, there is added to the charged vessel of step (A) above, with stirring 15–25 ml. of a mixture of trifluoroacetic acid, methylene chloride and mercaptoethanol (50:45:5;V/V/V). The resulting mixture is stirred for about 21 minutes, washed successively with methylene chloride, dioxane and then diluted with 20 ml of 5.5 N solution of hydrochloric acid in dioxane. The mixture is then shaken for about 15 minutes, and filtered. The residue is washed successively with dioxane, chloroform and then neutralized with 10 to 12% triethylamine in chloroform, washed with chloroform, then methylene chloride or dimethylformamide depending on the next solvent to be used.

(C) L-lysine Coupling

While maintaining the nitrogen gas atmosphere, three fold molar excess of resin capacity of benzyl-Boc-L-lysine [Lys (Z), Peninsula, supra.] dissolved in methylene chloride is added to the residue of step (B) above. The resulting mixture is shaken and after about 10 minutes, 3 fold molar excess of N,N-dicyclohexylcarbodiimide dissolved in 10–15 ml. of methylene chloride is added with stirring. The resulting mixture is shaken at room temperature for 4.5 to 5 hours. At the end of this period, the reaction mixture is filtered and the residue washed with methylene chloride, ethanol and dried.

(D) Deblocking of the Product of Step (C)

While maintaining the nitrogen atmosphere, the product of Step (C) is deblocked following the procedure of Step (B) above to obtain the product of formula:

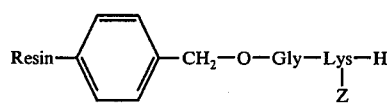

$$\text{Resin}\!-\!\!\bigcirc\!\!-\!CH_2\!-\!O\!-\!Gly\!-\!\underset{\underset{Z}{|}}{Lys}\!-\!H$$

where Z is the protective benzyl group.

(B) Coupling of Glutamine

To the product of Step (D) above there is added with mixing 4 molar excess of the p-nitrophenyl ester of Boc-L-glutamine [Gln (ON$_p$), Peninsula, supra.] dissolved in 15–20 ml. of dimethylformamide containing 1.5 M urea. The resulting mixture is shaken overnight, filtered, washed with dimethylformamide-ethanol mixture and dried.

(F) Deblocking of the Product of Step (E)

While maintaining the nitrogen atmosphere, the product of Step (F) above is deblocked following the procedure of Step (B) above to obtain a product of formula:

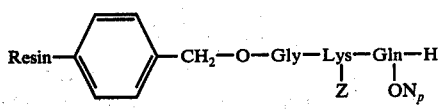

wherein Z is as previously defined and ON$_p$ represents the protective P-nitrophenyl ester group.

(G) Coupling of Tryptophan

While maintaining the nitrogen gas atmosphere, 3 fold molar excess of Boc-L-Tryptophan (Peninsula, supra.) dissolved in dimethylformamide and adjusted to 15 ml. with the addition of methylene chloride is added to the product of Step (F) above and the resulting mixture shaken. After about 10 minutes, 3 fold molar excess of N,N-dicyclohexylcarbodiimide is added and the resulting mixture is shaken for 4.5 to 5 hours at room temperature. At the end of this period, the reaction mixture is filtered and the residue washed with dimethylformamide. The washed residue is dried.

(H) Deblocking the Product of Step (G)

While maintaining the nitrogen atmosphere, the product of Step (G) is deblocked following the procedure of Step (B) above to obtain the product of formula:

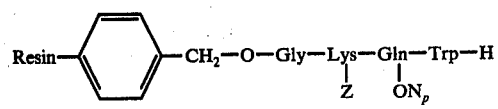

where Z and ON$_p$ are as before defined.

(I) Coupling of Serine

While maintaining the nitrogen gas atmosphere, 3 fold molar excess of the benzyl ester of Boc-L-serine [Boc-L-Ser (OBzl), Peninsula, supra] dissolved in 15 ml of methylene chloride is added to the residue of Step (H) above. The resulting mixture is shaken and after about 10 minutes, 3 fold molar excess of N,N-dicyclohexylcarbodiimide in 15–20 ml. of methylene chloride is added with stirring. The resulting mixture is shaken at room temperature for 4.5 to 5 hours. At the end of this period, the reaction mixture is filtered and the residue washed and dried.

(J) Deblocking of the Product of Step (I)

While maintaining the nitrogen atmosphere, the product of Step (I) above is deblocked following the procedure of Step (B) above to obtain a produce of formula:

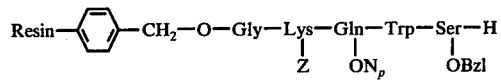

wherein Z and ON$_p$ are as previously defined; OBzl is the benzyloxy protective group.

(K) Coupling of Phenylalanine

While maintaning the nitrogen atmosphere, the product of Step (J) above is admixed with 3 fold molar excess of carbobenzoxy-L-phenylalanine [Boc-L-phenylalanine, Peninsula, supra.] dissolved in methylene chloride. The resulting mixture is shaken and after about 10 minutes, 3 fold molar excess of N,N-dicyclohexylcarbodiimide in 15 ml of methylene chloride is added with stirring. The resulting mixture is shaken at room temperature for 4.5 to 5 hours. At the end of this period, the reaction mixture is filtered and the residue washed and dried.

(L) Deblocking of the Product of Step (K)

While maintaining the nitrogen atmosphere, the product of Step (K) above is deblocked following the procedure of Step (B) above to obtain a product of formula:

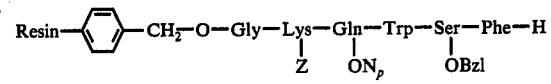

wherein Z, ON$_p$ and OBzl are as before defined.

(M) The above Steps C-L, inclusive, are repeated sequentially three additional times to obtain the product of formula:

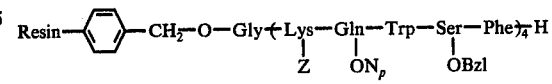

(N) The product of Step M above is admixed with 10 ml of dry hydrogen fluoride for 1 hour at a temperature of 0° C. in the presence of 1 ml of anisole. At the end of this period, the residue is separated from the hydrogen fluoride, washed several times with ether and then dried. The remaining residue is extracted with trifluorocetic acid and the extract neutralized with 5% sodium bicarbonate. The neutralized residue is then chromatographed on a column of Sephadex G-10 (3 × 100 cm). The column is equilibrated and the desired product eluted with 0.1 M acetic acid [method of Hashim et al., Biochem. Biophys. Res. Commun., 50,589, (1973a); Arch. Biochem. Biophys., 156, 287, (1973b)]. The product obtained is of the formula:

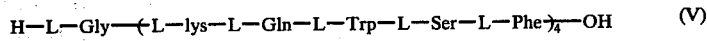

The purity of the product is established by chromatography and high voltage and polyacrylamide disc gel electrophoresis (method of Hashim et al., Archs. Biochem, Biophys., 129, 635-44, (1969). Amino acid analysis gives whole integers of expected residues.

EXAMPLE 2

(A)

A suitable reaction vessel is charged with 100 gms of carbo-t-butyloxy-L-lysine polymer containing from 0.25 to 0.5 moles of L-lysine per gram [Boc-L-lysine(Z)-resin ester, Peninsula, supra.]. The vessel is then vented and repeatedly pressured with nitrogen gas to remove all traces of air from the reaction vessel. The vent is then closed to maintain a nitrogen gas atmosphere in the reaction vessel.

(B) Deblocking the Starting Boc-L-lysine Resin Ester

The Boc-L-lysine resin ester charge of Step (A) above is deblocked following the procedure of Step (B), Example 1, supra.

(C) Coupling of Glutamine

To the product of Step (B) above, the P-nitrophenyl ester of Boc-1-Glutamine [Gln (ON$_p$), Peninsula, supra.] is coupled following the procedure of Step (E), Example 1, supra.

(D) Deblocking of the Product of Step (C)

The procedure of Step (B), Example 1, supra., is followed to obtain the product of formula:

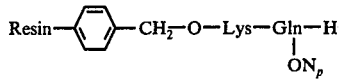

where ON$_p$ represents the protective p-nitrophenyl group.

(E) Coupling of L-glycine

The product of Step (D) above is reacted with Boc-L-glycine according to the procedure of Step C, Example 1, above, and the product thereof deblocked according to Step B of Example 1, supra. to obtain a product of formula:

Resin—⟨⟩—CH$_2$—O—Lys—Gln—Gly—H
                              |
                              ON$_p$

(F)

The procedure of Step E above is repeated 3 additional times to obtain a product of formula:

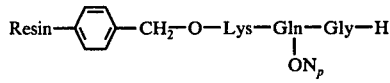

(G) Coupling of Tryptophan

L-tryptophan is coupled to the product of Step (F) above, following the procedure of Step (G), Example 1, supra. The product is deblocked to obtain a product of formula:

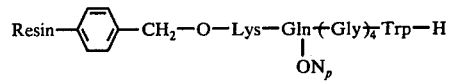

(H)

Step (E) above is repeated twice, starting with the product of Step (G) above, to obtain a product of formula:

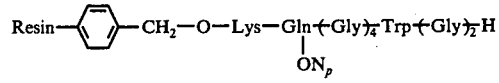

(I)

The product of Step (H) above is treated according to the procedure of Step (N), Example 1, supra to obtain a final product of formula:

H⟨L—Gly⟩$_2$L—Trp⟨L—Gly⟩$_4$L—Gln—L—Lys—OH  (IX)

From the foregoing examples, it will be obvious to those skilled in the art how the compounds (I) of the invention may be prepared by selection of the appropriate sequence of reactions, employing the known blocked or amino function protected L-amino acids and the well-known starting L-amino acid resin esters. Thus, the foregoing general procedure of Examples 1 and 2 are followed, employing the appropriate Boc-L-amino acids, to obtain the following compounds, representative of those of the Formula (I).

H — Gln — Lys — OH;

H — Gln — Arg — OH;

H — Gln — His — OH;

H — Trp — Gln — Lys — OH;

H — Gly — Gln — Lys — OH;

H — Gly — Trp — Gln — Lys — OH;

H⟨Gly—Gln—Lys⟩$_2$OH;

H—Gly⟨Gly—Gln—Lys⟩$_2$OH;

H—Gly⟨Gly—Gln—Lys⟩$_2$OH;

H⟨Gly⟩$_2$Trp⟨Gly⟩$_4$Gln—Arg—OH;

H⟨Gly⟩$_2$Tyr⟨Gly⟩$_4$Gln—Lys—OH;

H⟨Gly⟩$_2$Tyr⟨Gly⟩$_4$Gln—Arg—OH;

H⟨Gly⟩$_2$Trp⟨Gly⟩$_4$Gln—His—OH;

H⟨Gly⟩$_2$Tyr⟨Gly⟩$_4$Gln—His—OH;

H⟨Gly⟩$_2$Trp—Gly—Gly—Lys⟨Gly⟩$_2$Trp—Gly—Gln—Lys—OH;

and the like.

Albumin, gamma globulin and like polypeptides, both synthetic and natural, may be reacted with the -OH group at the C-terminal position of the above formulae to obtain a greater molecular weight, act as a carrier to prevent accelerated decay and enhance the immune response to the synthetic peptide after it has been administered, and allow the peptide to attach to and block sensitized cells from doing further damage. The method of preparation is that described above. See also Merrifield, supra. Thus, there is obtained those compounds (I) of the invention having the more specific formula:

H—Gly—Gly—Trp$\overline{+}$Gly$\overline{+_4}$Gln—Lys—albumin;

H—Gly—Gly—Trp$\overline{+}$Gly$\overline{+_4}$Gln—His—albumin;

H—Gly—Gly—Trp$\overline{+}$Gly$\overline{+_4}$Gln—Arg—albumin;

H$\overline{+}$Gly$\overline{+_4}$Tyr$\overline{+}$Gly$\overline{+_4}$Gln—Lys—albumin;

H$\overline{+}$Gly$\overline{+_4}$Tyr$\overline{+}$Gly$\overline{+_4}$Gln—His—albumin;

H$\overline{+}$Gly$\overline{+_4}$Tyr$\overline{+}$Gly$\overline{+_4}$Gln—Arg—albumin;

H—Gly—Gly—Trp [ Gly ]$_4$ Gln—Lys—gamma globulin;

H—Gly—Gly—Trp$\overline{+}$Gly$\overline{+_4}$Gln—His—gamma globulin;

H—Gly—Gly—Trp$\overline{+}$Gly$\overline{+_4}$Gln—Arg—gamma globulin;

H$\overline{+}$Gly$\overline{+_4}$Tyr$\overline{+}$Gly$\overline{+_4}$Gln—Lys—gamma globulin;

H$\overline{+}$Gly$\overline{+_4}$Tyr$\overline{+}$Gly$\overline{+_4}$Gln—His—gamma globulin;

H$\overline{+}$Gly$\overline{+_4}$Tyr$\overline{+}$Gly$\overline{+_4}$Gln—Arg—gamma globulin;

H—Gly—Trp—Gly—Gln—Lys—Gly—Trp—Gly—
—Gln—Lys—gamma globulin;

and the like.

When the synthetic compound of formula (I) is in the form of a tripeptide $R_2$-Gln-$R_4$ that is where $b$, $c$ and $m$ in the formula (I) are O, the tripeptide is made following the procedure of Merrifield supra. When more than one of such tripeptides are linked together, that is, when $n$ of formula (I) is greater than 1 the resulting polypeptide is made following the procedure of Messrs. Hirshmann R., et al, Journal of the American Chemical Society, Vo. 91, p. 507, (1969). Such peptides following this procedure may be represented as H$\overline{+}$Trp—Gln—Lys$\overline{+_n}$OH; H$\overline{+}$Trp—Gln—Arg$\overline{+_n}$OH;

H$\overline{+}$Trp—Gln—His$\overline{+_n}$ OH; H$\overline{+}$Tyr—Gln—Lys$\overline{+_n}$OH;

H$\overline{+}$Tyr—Gln—Arg$\overline{+_n}$OH; and

H$\overline{+}$Tyr—Gln—His$\overline{+}$OH.

When administered, these tripeptides prevent cells destined to produce disease, from producing pathologic damage to the nervous tissues in mammals.

EXAMPLE 3

Parenteral Aqueous Suspension

A sterile aqueous suspension for parenteral administration containing 0.5 mg. of a synthetic compound of formula:

H — Phe — Ser — Trp — Gln — Lys ]$_4$ Gly — OH  (compound V)

in each 1 ml. is prepared from the following types and amounts of ingredients:

Compound V, Example 1, supra. 0.5 gm
polysorbate 80: 8 gms
sodium chloride: 18 gms
benzyl alcohol: 18 gms
water for injection q.s.: 1000 ml A dose of 1/10 ml. administered subcutaneously to a mammal is useful for diagnosis of multiple sclerosis in multiple sclerosis afflicted mammals.

Experiments Relative to Non-Disease Inducing Characteristics

EXAMPLE 4

In the following tables experiments are conducted on test animals using the synthetic compounds of the invention in varying dosage units. The synthetic compounds (I) administered to all the test animals, guinea pigs (Table 1), rabbits (Table 1A) and rats (Table 1B) is of the formula:

$$H - (Gly)_2 - Trp - (Gly)_4 - Gln - Lys - OH. \quad (IX)$$

Prepared according to Example 2, supra. The synthetic peptide (IX) is administered subcutaneously to guinea pigs, rabbits and rats at concentrations of 10, 100, 250, 500 and 1500 micrograms as a single dose in complete Freund's adjuvant as the carrier, for the purpose of determining whether or not the synthetic compound (IX) is non-encephalitogenic. None of the animals showed any clinical signals of disease within the expected time, i.e. less than 20 days. These signs include loss of weight, tremors and incontinence (see Tables 1, 1A and 1B). In Tables 1, 1A and 1B the Group III animals represent the control groups in which the animals are injected with only the complete Freund's adjuvant. Complete Freund's adjuvant is sold by the Difco Company under catalogue number 0638-60-7 Bacto Adjuvant Complete Freunds. None of the animals exhibit any signs of disease. The Group IV animals of tests 1 and 1A are administered the native peptide of formula:

H — Phe — Ser — Trp — Gly — Ala — Glu — Gly
— Gln — Lys — OH  (X)

and are not administered any of the synthetic compound (I). In Table 1B the Group IV animals are administered basic protein, a polypeptide isolated from bovine myelin protein and are not administered any of the synthetic compound (I). The disease is induced in all of the Group IV test animals.

Generally 10-15 microgram doses of the native peptide, i.e. formula (X) induces the disease in less than 20 days and death results 2-3days post onset of signs. The animals are observed for more than 90 days. During this time the animals remain healthy and their growth rate is not different from the normal. As noted above, the control animals are given only the carrier adjuvant. Histological examination of brain and spinal cord sections from each animal including the control animals show the absence of lesions characteristic of the disease but lesions characteristic of the disease are evident from similar sections taken from Group IV animals.

TABLE I

| Group No. | Guinea Pigs | | | |
| --- | --- | --- | --- | --- |
|  | I | II | III | IV |
| No. of Animals | 15 | 15 | 15 | 15 |
| Dose Formula (IX) | 10 μg | 500 μg | 0 | 0 |
| Formula (X) |  |  |  | 20 μg |
| Clinical Disease |  |  |  |  |

TABLE I-continued

| | Guinea Pigs | | | |
|---|---|---|---|---|
| Group No. | I | II | III | IV |
| Score | | | | |
| 30 days | 0/15 | 0/15 | 0/15 | 14/15 |
| 90 days | 0/15 | 0/15 | 0/15 | 15/15 |
| Formula (IX) H$(\text{Gly})_2$Trp$(\text{Gly})_2$Gln—Lys—OH | | | | |
| Formula (X) H—Phe—Ser—Trp—Gly—Ala—Glu—Gly—Gln—Lys—OH | | | | |

TABLE 1A

| | Rabbits | | | |
|---|---|---|---|---|
| Group No. | I | II | III | IV |
| No. of animals | 10 | 10 | 10 | 15 |
| Dose Formula (IX) | 500 μg | 1500 μg | 0 | 0 |
| Formula (XI) | | | | 50 μg |
| Clinical Disease Score | | | | |
| 30 days | 0/10 | 0/10 | 0/10 | 12/15 |
| 90 days | 0/10 | 0/10 | 0/10 | 13/15 |

TABLE 1B

| | Lewis Rats | | | |
|---|---|---|---|---|
| Group No. | I | II | III | IV |
| No. of Animals | 10 | 10 | 10 | 10 |
| Dose Formula (IX) | 100 μg | 250 μg | 0 | 0 |
| *Basic Protein | | | | 50 μg |
| Clinical Disease Score | | | | |
| 30 days | 0/10 | 0/10 | 0/10 | 8/10 |
| 90 days | 0/10 | 0/10 | 0/10 | 10/10 |

* Basic protein is the native protein isolated from bovine myelin known to induce disease (EAE) in at least 50% in mammals such as guinea pigs, rats and rabbits when administered subcutaneously at dosage levels of 10 μg or more.

It can be seen from the results given in Tables 1, 1A and 1B, that the synthetic peptide of formula (IX) is inactive and does not induce disease when administered to the test animals of Groups I and II when compared to the control group of test animals Group III. However, it can be seen from Tables 1, 1A and 1B that the disease is induced in Group IV animals when administered the native peptide of formula (X) or (XI), infra., or the native peptide found in basic protein. It can be concluded that the synthetic compounds (I) of the invention herein does not induce disease and are non-EAE producing.

The above experiment is repeated using similar experimental settings and test animals, i.e. guinea pigs, rabbits and rats in which the conditions were maintained to that of the foregoing experiment. The only change in each test is the substitution of a different synthetic peptide material of the invention herein, i.e.; those compounds specifically named in the prior examples herein for the formula (IX). The results obtained using such compounds are identical to the results obtained using formula (IX). None of the animals exhibit any clinical signs of disease within the expected time period, i.e.; less than 20 days. None of the animals loose weight or show signals of tremors or incontinence. However, those animals of Group IV administered the native material specified, i.e.; the encephalitogenic disease inducing material come down with the disease.

EXAMPLE 4

Non-Encephalitogenic Properties of Preferred Compound V

A number of guinea pigs are divided into equal groups I, II, III, IV, V, VI and VII. Each of groups I, II, III and IV are given a single subcutaneous administration of the compound (V) (formula: H — Phe — Ser — Trp — Gln — Lys )$_4$Gly — OH) prepared according to Example 1. supra. The dose administered, in Complete Freund's adjuvant and the disease index (number of animals showing disease symptons/number tested) obtained after 30 and 120 days, respectfully, are given in Table II below. Groups, V, VI and VII serve as controls. Group V received a single administration of the myelin basic protein (BP), group VI received a single administration of peptide E (E), the encephalitogenic region derived from the encephalitogenic basic protein. Group VII received a single administration of Complete Freund's adjuvant alone.

TABLE 11

| | Compound V | | | | BP | E | Control |
|---|---|---|---|---|---|---|---|
| Group No. | I | II | III | IV | V | VI | VII |
| No. of Guinea Pigs | 20 | 30 | 15 | 10 | 10 | 10 | 10 |
| Sensitizing mg antigen/CFA | 0.500 | 0.100 | 0.025 | 0.005 | 0.025 | 0.025 | CFA |
| Disease Index | | | | | | | |
| Day 30 | 0/10 | 0/20 | 0/15 | 0/10 | 9/10 | 10/10 | 0/10 |
| Day 120 | 0/10 | 0/10 | | | | | |

The figures show the number of diseased guinea pigs per number tested. The disease index for experimental allergic encephalomyelitis (EAE) is reported in terms of clinical and histophathological criteria by day 30 following sensitization. Also, in case of delayed onset of disease, 10 animals from groups number I and II were observed for a period of 120 days. The example shows the non-encephalitogenic nature of a preferred compound (I) of the invention.

EXAMPLE 5

Specificity of Compound V — Induced Delayed Type Skin Hypersensitivity Response

Guinea pigs are sensitized (10 animals/group) with 500 μg each of compound (V) (prepared according to Example 1, supra.), myelin basic protein (BP), the alpha -1 component of calf skin ($\alpha 1$ — calf) and the alpha -1 component of guinea pig collagen ($\alpha 1$ — g.p.), emulsified in complete Freund's adjuvant. At day 11 after sensitization, the animals were skin tested with various doses of the specific antigens dissolved in saline. Positive responses are indicated by erythema at the skin test site. A control group is administered saline.

The number of guinea pigs tested, the dose of antigen, and the erythema elicited (measured in mm) is given in Table III below.

Table III

| Sensitizing antigen | Compound V | $\alpha_1$-calf | $\alpha_1$-g.p. | BP | Saline (control) |
|---|---|---|---|---|---|
| dose (μg) | 500 | 500 | 500 | 500 | CFA |
| No. animals/group | 10 | 10 | 10 | 10 | 10 |
| Skin testing antigen | dose (mg) | | mm erythema of skin test site | | |
| Compound (V) | 0.005 | 10×10 | 2×2 | 2×2 | 7×7 | 0×0 |
| BP | 0.025 | 10×10 | 2×2 | 2×2 | 12×12 | 0×0 |
| $\alpha_1$-calf | 0.100 | 2×2 | 13×14 | 13×14 | 2×2 | |
| $\alpha_1$-g.p. | 0.100 | 2×2 | 13×14 | 13×14 | 2×2 | 0×0 |

The specificity of the reaction is shown by the ability of compound V and BP to elicit positive delayed skin responses in animals sensitized with compound V and BP and negative skin responses in animals sensitized with the $\alpha_1$-calf or $\alpha_1$-g.p. component of skin collagen. Further, the $\alpha_1$-calf and the $\alpha_1$-g.p., which induce delayed type skin hypersensitivity in guinea pigs, did not elicit skin hypersensitivity responses in guinea pigs sensitized either with peptide (V) or with myelin basic protein.

EXAMPLE 6

Delayed Type Skin Hypersensitivity Response

Guinea pigs are sensitized (10 animals/group) with varying doses of the compound (V) (prepared according to Example 1, supra.) administered subcutaneously in Complete Freund's adjuvant, incomplete Freund's adjuvant and saline. At various times following this administration, the animals were skin tested with various doses of compound (V) in saline. The sensitizing doses, carriers, times of skin-testing, test doses and erythema elicited are given in Table IV below.

TABLE IV

| Sensitizing antigen | | Compound (V) | | | | | | Control |
|---|---|---|---|---|---|---|---|---|
| dose (mg) | | 0.500 | 0.100 | 0.025 | 0.005 | 0.500 | 0.500 | saline |
| adjuvant | | CFA | CFA | CFA | CFA | IFA | saline | CFA |
| No. animals/group | | 10 | 10 | 10 | 10 | 10 | 10 | 10 |
| Days after sensitization | skin test dose of Compound (V) | mm erythema of skin test sites | | | | | | |
| 4 | 0.005 | 9×9 | 5×5 | 3×3 | 2×2 | 6×5 | 4×4 | 0×0 |
| 8 | 0.005 | 11×12 | | | | | | |
| 13 | 0.005 | 10×10 | 10×10 | 9×10 | | 4×4 | 4×4 | 0×0 |
| 21 | 0.005 | 18×19 | 11×11 | | | | | 0×0 |

Compound (V) is shown to be antigenic and induces delayed type hypersensitivity (DTH) in mammals. The extent of the DTH response is dose related. Compound (V) induces DTH response regardless of whether the carrier is Complete Freund's adjuvant (CFA), incomplete Freund's adjuvant (IFA) or physiological saline (saline). The values shown are the average skin response of 10 animals in each group. The numbers shown are measurements of the cross-sectional diameters of the erythematous area recorded at 24 hours following the skin test.

Prevention Type Experiments

EXAMPLE 7

In Table V, prevention type experiments are conducted on guinea pigs, rats and rabbits using the synthetic compounds of the invention herein and using varying dosages of formula (IX).

Three groups of test animals are set up, each group including two control groups with an identical number of animals. In each case the animals of control groups B are administered only the carrier and are not immunized with formula (IX).

At day zero group I animals except group 1B guinea pigs are injected subcutaneously with 250 micrograms of formula (IX) emulsified in incomplete Freund's adjuvant as carrier. Incomplete Freund's adjuvant is sold by the Difco Company under catalogue number 0639-60-6 Bacto Adjuvant.

Group II animals except group IIB rats are injected subcutaneously with 150 micrograms of formula (IX) dissolved in saline.

Group III animals except group IIIB rabbits are injected intraveneously with 1500 micrograms of formula (IX).

The above procedure is followed by daily for 14 consecutive days. Each animal in group I except group IB receive 14 injections of 250 micrograms for a total of 3500 micrograms. Each animal in group II except group IIB receive 14 injections of 150 micrograms for a total of 2100. Each animal in group III except group IIIB receive 14 injections of 1500 micrograms for a total of 21,000 micrograms. At day 7 all of the group I animals except group IB are challenged with 25 micrograms of the disease inducing peptide of formula (X); group II animals, except group LLA, are challenged with 150 μg of bovine basic protein isolated from myelin protein and group III animals, except group IIIA, are challenged with 50 μg of native compound of formula:

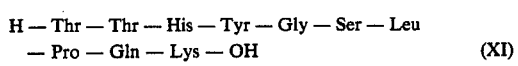

$$H - Thr - Thr - His - Tyr - Gly - Ser - Leu$$
$$- Pro - Gln - Lys - OH \qquad (XI)$$

All animals of control group B which are injected with the disease inducing peptide begin to show clinical evidence of disease in 12 to 14 days. Eighty to ninety percent of these animals died by day 20. In all cases the untreated control group A show no evidence of disease. The animals of groups I, II and III which are treated with formula (IX) prior to being challenged with the disease inducing peptide as indicated in Table II show no clinical evidence of the disease and remain healthy for 90 days at which time they are sacrificed.

Pretreatment of the animals with formula (IX) induced the sensitization of cells with the synthetic disease non-inducing peptide which allows the sensitized cells to recognize any agent with the same structural characteristics. Thus, when the disease inducing peptide or the native basic protein is administered at day 7 it is recognized by the synthetic peptide sensitized cells and prevents the native materials from inducing the disease as it does in the group B test animals.

TABLE V

| | Prevention of Disease in Mammals | | | | | | | | |
|---|---|---|---|---|---|---|---|---|---|
| | Guinea Pigs | | | Rats | | | Rabbits | | |
| Group | I | IA | IB | II | IIA | IIB | III | IIIA | IIIB |
| No. of Animals | 15 | 15 | 15 | 15 | 15 | 15 | 15 | 15 | 15 |
| Day 0–14 | 250 μg Formula IX | 250 μg Formula IX | 0 | 150 μg Formula IX | 150 μg Formula IX | 0 | 1500 μg Formula IX | 1500 μg Formula IX | 0 |
| Day 7 | 25 μg Formula X | 0 | 25 μg Formula X | 50 μg B.P.* | 0 | 50 μg B.P.* | 50 μg Formula XI | 0 | 50 μg Formula XI |
| Clinical | | | | | | | | | |

TABLE V-continued

| | Prevention of Disease in Mammals | | | | | | | | |
|---|---|---|---|---|---|---|---|---|---|
| | Guinea Pigs | | | Rats | | | Rabbits | | |
| Group | I | IA | IB | II | IIA | IIB | III | IIIA | IIIB |
| Disease Score | | | | | | | | | |
| Day 37 | 0/10 | 0/15 | 13/15 | 0/15 | 0/15 | 13/15 | 0/15 | 0/15 | 12/15 |
| Day 97 | 0/15 | 0/15 | 13/15 | 0/15 | 0/15 | 13/15 | 0/15 | 0/15 | 13/15 |

Formula IX : H-Gly-Gly-Trp-Gly-Gly-Gly-Gly-Gln-Lys-OH
Formula X : H-Phe-Ser-Trp-Gly-Ala-Glu-Gly-Gln-Lys-OH
Formula XI : H-Thr-Thr-His-Tyr-Gly-Ser-Leu-Pro-Gln-Lys-OH
NOTE:
All animals in groups 1A and 1B were administered 250 μg of incomplete Freund's adjuvant (IFA) daily for 14 days. All animals in groups IIA and IIB were administered 150 μg of isotonic saline daily for 14 days. Group III animals were not injected with any carrier.
*Basic Protein identified above (see Eylar et al., supra.)

Suppression Type Experiments

EXAMPLE 8

In Table VI below, suppression type experiments are conducted on guinea pigs to show the effect of administering the disease producing native peptide (formula X). The animals are injected with the synthetic compounds IX of the invention herein at varying periods after the initial injection of the native peptide and using varying dosages.

Four groups of guinea pigs are employed. Group IV animals received neither the disease inducing native peptide (formula X) nor the synthetic compound (IX) of the invention and served as a second control group. Group III animals are treated with the native peptide (formula X) only at day zero by the injection of 25 micrograms emulsified in complete Freund's adjuvant and served as a first control group. Group I animals are injected with 25 micrograms of the disease inducing native peptide (formula X) emulsified in complete Freund's adjuvant at day zero. Also, group I animals received daily injections for 14 consecutive days of 250 micrograms each of formula I dissolved in saline administered intraveneously, the first injection being administered starting day zero. Group II animals receive the identical treatment of group I animals except group II animals receive the initial injection of formula 1 at day 7 and continued daily for 14 consecutive days, each injection containing 250 micrograms of formula (IX) in saline for a total of 3,500 micrograms.

Eighty percent of the first control group show evidence of disease within 16 days post sensitization and die by day 20. The second control group remains healthy throughout the experiment. Experiment groups I and II loose about 10% of body weight at day 14–16 and begin to gain weight thereafter. No other clinical symptoms of the disease are apparent in experimental groups I and II for a period of three months after which they are sacrificed.

TABLE VI

| | Suppression of Disease in Guinea Pigs | | | |
|---|---|---|---|---|
| Group No. | I | II | III | IV |
| No. of Animals | 15 | 15 | 15 | 15 |

TABLE VI-continued

| | Suppression of Disease in Guinea Pigs | | | |
|---|---|---|---|---|
| Group No. | I | II | III | IV |
| Day 0 (formula X) | 25 μg | 25 μg | 25 μg | 0 |
| Day 0–14 (formula IX) | 250 μg | 0 | 0 | 0 |
| Day 7–21 (formula IX) | 0 | 250 μg | 0 | 0 |
| Clinical Disease Score | | | | |
| 16 Days | 0/15 | 0/15 | 12/15 | 0/15 |
| 30 Days | 0/15 | 0/15 | 12/15 | 0/15 |
| 90 Days | 0/15 | 0/15 | 12/15 | 0/15 |

In this type experiment, the disease inducing peptide compound administered at day 0 results in the formation of sensitized cells which in turn give rise to clinical symptoms of the disease. However, when compound (IX) of the invention is administered as the synthetic peptide analogue to the disease inducing native peptide (formula X), the sensitized cells recognize the synthetic peptide and suppress further or continued induction of the disease of the invention herein. The continued treatment is effective in neutralizing or immunizing the disease inducing cells as they become sensitized. This approach is the reverse of that shown for preventing type experiment in which the treatment prevents cells from becoming disease inducing.

EXAMPLE 9

In table VII below, guinea pigs of Groups No. 1–11, inclusive, are challenged with Freund's complete adjuvant (FCA) emulsion of either a compound (V) (Groups 1–3) or bovine basic protein (BP) (Groups 4–11). Groups 1, 2 and 3 receives no further treatment. For Groups 4 and 5, the suppressive treatment in Freund's incomplete adjuvant (FIA) is started on day 8 before the appearance of clinical signs of experimental allergic encephalomyelitis (EAE) and is continued through day 17. For Groups 6, 7 and 8 the treatment begins the day hind leg paralysis is observed and is continued for 10 consecutive days. Surviving animals are killed on day 32 for histological examination of the brain and spinal cord tissue. Treatment consists of daily subcutaneous injections after challenge. The challenge, treatment and results are shown in Table VII below:

TABLE VII

| Group No. | Challenging antigen (μg per FCA) | Treatment FIA | Clinical EAE | Reversal clinical EAE | Histological EAE |
|---|---|---|---|---|---|
| 1 | 25 μg Compound V | None | 0/15 | None | 0/15 |
| 2 | 100 μg Compound V | None | 0/10 | None | 0/15 |
| 3 | 5,000 μg Compound V | None | 0/10 | None | 0/10 |
| 4 | 100 μg BP | 1 mg Compound V | 2/4 | 2/4 | 2/4 |
| 5 | 100 μg BP | FIA | 4/4 | 0/4 | 4/4 |
| 6 | 150 μg BP | 2.5 mg Compound V | 5/5 | 5/5 | 2/5 |
| 7 | 150 μg BP | FIA | 5/5 | 0/5 | 5/5 |

TABLE VII-continued

| Group No. | Challenging antigen (μg per FCA) | Treatment FIA | Clinical EAE | Reversal clinical EAE | Histological EAE |
|---|---|---|---|---|---|
| 8 | 150 μg BP | saline | 6/6 | 0/6 | 6/6 |
| 9 | 150 μg BP | 4.0 mg Compound V | 7/7 | 6/7 | 4/7 |
| 10 | 150 μg BP | 1 mg BP | 4/4 | 2/4 | 3/4 |
| 11 | 150 μg BP | FIA | 7/7 | 0/7 | 7/7 |

As shown in Table VII, treatment with compound (V) significantly reduced the incidence of disease compared with Freund's incomplete adjuvant (FIA) treated controls (compare groups 4 and 5). Daily treatment of animals in group 6 with 2.5 mg compound (V) for 10 consecutive days was sufficient to reverse tremor and hind leg paralysis in addition to lethargy and weight loss in the five treated animals. Histological examination of the brain and spinal cord tissues on day 32 after challenge revealed the presence of EAE lesions in 2 out of 5 of the animals in spite of the complete reversal of the clinical signs of EAE. Control guinea pigs similarly treated with FIA or saline (groups 7 and 8) died between days 10 and 14 or were killed because of severe paralysis.

Compound V induced reversal of clinical signs of EAE was further studied in an advanced stage of the disease. The treatment for guinea pigs in group 9 was initiated on the second day after the onset of hind leg paralysis. Within 4-6 treatment days, paralyzed animals regained the use of their hind legs and were able to run about the cage; however, one of seven guinea pigs died after the second treatment without evidence of improvement in his disease state. In contrast, treatment of group 10 with 1 mg bovine BP was partially successful in reversing the disease at this late stage of development. None of the FIA-treated controls, group 11, recovered from EAE.

The use of Compound V is advantageous in view of its non-encephalitogenic properties and its ability to interact specifically with disease-inducing cells and thus to inhibit the development of EAE and reverase a full-blown stage of disease.

Certain derivative compounds of the compounds (I) of the invention also possess the biological activity associated with the compounds (I) of the invention and are within the scope of the invention. Representative of such derivative compounds are the acylate derivatives, i.e.; compounds where one or more of the hydroxyl, amino and/or amino groups on the molecule of the compound (I) are acylated. Acylation of the hydroxyl, amino or imino groups, including the N-terminal amino group may be carried out by conventional and well-known techniques. For example, by reacting the hydroxyl, amino or imino groups of the compounds (I) with an acylating agent such as an acyl halide of the formula:

$$R'-\overset{O}{\underset{\|}{C}}-Z \quad (XI)$$

wherein Z represents halogen such as chlorine, bromine and iodine and

is a carboxylic acid acyl radical, advantageously a hydrocarbon carboxylic acid acyl of not more than 18 carbon atoms; or halo-, nitro-, hydroxy-, amino-, cyano-, thiocyano-, or lower alkoxy- substituted hydrocarbon carboxylic acid acyl radical advantageously of not more than 18 carbon atoms. Representative of carboxylic acid acyl radicals are the acyl radicals of the following acids:

(a) saturated or unsaturated, straight or branched chain aliphatic carboxylic acids, for example acetic, propionic, butyric, isobutyric, tert-butylacetic, valeric, isovaleric, caproic, caprylic, succinic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, methylcyclopentenecarboxylic acid, cyclohexanecarboxylic acid, dimethylcyclohexenecarboxylic acid, dipropylcyclohexanecarboxylic acid, and the like; (c) saturated or unsaturated, alicyclic aliphatic carboxylic acids, for example cyclopentanepropionic acid cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzic acid, and the like; and (e) aromaticaliphatic carboxylic acids, for example, phenylacetic acid, phenylpropionic acid, phenylvaleric acid, cinnamic acid, phenylpropionic acid and naphthylacetic acid, and the like. Suitable halo-, nitro-, hydroxy-, amino-, cyano-, thio-, cyano-, and lower alkoxyhydrocarbon carboxylic acids include hydrocarbon carboxylic acids as given above which are substituted by one or more of halogen, nitro, hydroxy, amino, cyano, or thiocyano, or loweralkoxy, advantageously loweralkoxy of not more than 18 carbon atoms, for example, methoxy, ethoxy, propoxy, butoxy, amyloxy, hexyloxy, and isomeric forms thereof. Examples of such substituted hydrocarbon carboxylic acids are mono-, di-, and trichloroacetic acid;
α and β-chloropropionic acid
α and γ-bromobutyric acid;
α and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
6-bromo-2-methylcyclohexanecarboxylic acid;
2,3-dibromo-2-methyl-cyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;

3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicylic acid;
p-hydroxybenzoic acid;
β-resorcyclic acid;
gallic acid;
veratric acid;
trimethoxybenzoic acid;
trimethoxycinnamic acid;
4,4'-dichlorobenzilic acid
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate);
butyloxyformic acid;
pentyloxyformic acid;
hexyloxyformic acid;
dodecyloxyformic acid;
hexadecyloxyformic acid; and the like.

Alternatively the acid anhydrides, where available, may be used to acylate the compounds (I) of the invention.

The acylation is advantageously carried out by admixture of the acylating halide or anhydride with the compound (I) in the presence of an acid binding agent, for example a tertiary amine. Illustrative of tertiary amines which may be used are pyridine, quinoline, trimethylamine, triethylamine and the like. Advantageously the acylation is carried out in the presence of an inert solvent, i.e.; a solvent for the acylating agent which does not interfere with or alter the desired course of the acylation. Representative of such inert solvents are chloroform, ether, dimethyl formamide and the like.

Also within the scope of the invention are the ester derivatives of the compounds (I) obtained by reaction of an alcohol with the C-terminal carboxyl group of the compounds (I) of the invention, i.e.; a compound of the formula:

$$H\text{---}(A)\text{---}(B)_x\text{---}O\text{---}R'' \qquad (XII)$$

wherein A, B and X are as previously defined and R" is the residue of an alcohol. The esterification may be carried out by conventional and known procedures well known to those skilled in the art.

In general, the esterification comprises the reaction of an alcohol with the compound (I) after protection of amine groups with a protective group removable by hydrogenolysis. Following esterification, the protective group is removed to obtain the desired ester.

Representative of alcohols which may be used to obtain the desired ester derivative are lower alkanols such as methanol, ethanol, n-propanol, isopropanol, n-butanol, sec-butanol, t-butanol, n-pentanol, hexanol and the like; aralkanols such as benzyl or benzhydryl alcohol and the like; substituted aralkanols such as p-nitrobenzyl alcohol, p-methoxy-benzyl alcohol, 2,4,6-trimethylbenzyl alcohol and the like.

Preferred alcohols for preparing the esters of the compounds (I) are mono- or polyfunctional alcohols of higher molecular weight such as octanol, decanol, dodecanol, stearyl alcohol, octanediol, ribose, sucrose, sorbitol, glucose, mannitol and the like including isomeric forms thereof.

The novel compounds (I) of the invention and derivatives thereof exist either in the non-protonated (free base) form or in the protonated (acid addition salt) form, depending on the pH of the environment. They form stable protonates, i.e.; acid addition salts, on neutralization of the free base with suitable acids. Salts of the compounds (I) are made by neutralizing the free base with the appropriate acid to below about pH 7.0 and advantageously to about pH 2 to pH 6. Suitable acids for this purpose include hydrochloric, sulfuric, phosphoric, thiocyanic, gluosilicic, acetic, succinic, citric, lactic, maleic, fumaric, pamoic, cholic, palmitic, mucic, camphoric, glutaric, glycolic, phthalic, tartaric, lauric, stearic, salicylic, 3-phenylsalicyclic, 5-phenylsalicyclic, 3-methylglutaric, orthosulfobenzoic, cyclohexanesulfamic, cyclopentanepropionic, 1,3-cyclohexanedicarboxylic, 4-cyclohexenecarboxylic, octadecenylsuccinic, octenylsuccinic, methanesulfonic, benzenesulfonic, helianthic, Reinecke's, azobenzenesulfonic, octadecylsulfuric, picric and like acids. Conversely, the free base of compounds (I) are obtained from the corresponding salt, for example from the hydrochloride or sulfate salt, by dissolving or suspending the salt in buffer at about pH 5 to 7, preferably about pH 6, extracting with an immiscible organic solvent, for example chloroform, drying the extract, for example with anhydrous sodium sulfate, and removing the solvent by evaporation.

Acid addition salts of the compounds (I) of this invention may be used to upgrade the free bases, namely, by making acid addition salts of the free bases, subjecting them to purification procedures and then converting the salts back to the free bases by neutralizing with an alkali or contacting with an anionic resin, advantageously to about pH 7.5 to 8.5.

The pharmaceutically acceptable acid addition salts may be used for the same purposes as the free base. Illustrative of pharmaceutically acceptable acid addition salts are those formed upon reaction of the compounds (I) with hydrochloric acid, hydrobromic acid, sulfuric acid, phosphoric acid, acetic acid, lactic acid, citric acid succinic acid, benzoic acid, salicylic acid, pamoic acid, cyclohexanesulfamic acid and the like.

What is claimed:

1. The method of treating a mammal for the prevention, suppression and diagnosis of multiple sclerosis, which comprises; administering parenterally to said mammal from about 0.0001 to about 25 mg. per kilogram of body weight of a synthetic compound of the formula:

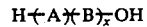

wherein x is an integer of at least 0 and A and B each represent a divalent moiety of the formula:

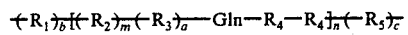

wherein $R_1$ and $R_5$ are each selected from the residue of an amino acid and the residue of a polypeptide; $R_2$ is selected from the residue of tryptophan and tyrosine; $R_3$ represents the residue of an amino acid; $R_4$ is selected from the residue of lysine, arginine and histidine; a is an integer of from 0 to 4, inclusive; b and c are each integers of at least 0; m is an integer of from 0 to 1, inclusive;

and $n$ is an integer of at least 1; provided that when $x$ is 0 then at least one of $R_1$ and $R_5$ is the residue of a polypeptide and when $R_1$ is the residue of a polypeptide $b$ is 1 and when $R_5$ is the residue of a polypeptide, $c$ is 1.

2. The method of claim 1 wherein said compound is selected from those of the formulae:

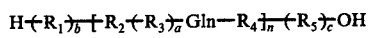  (a)

and

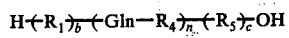  (b)

wherein $R_1$, $R_2$, $R_3$, $R_4$, $R_5$, $a$, $b$, $c$ and $n$ are as defined in claim 1, further provided that at least one of $R_1$ and $R_5$ is the residue of a polypeptide.

3. The method of claim 2 wherein one of $R_1$ and $R_5$ is the residue of an alpha-amino acid selected from the group consisting of tryptophan and tyrosine.

4. The method of claim 2 wherein $R_1$ is the residue of tyrosine.

5. The method of claim 1 wherein one of said $R_1$ and $R_5$ is the residue of albumin.

6. The method of claim 1 wherein one of said $R_1$ and $R_5$ is the residue of gamma globulin.

7. The method of claim 1 wherein said mammal is a human.

8. The method of claim 1 wherein from about 0.5 mg. to about 5.0 mg. per kg of body weight of the recipient mammal is administered for the prevention of multiple sclerosis in said mammal.

9. The method of claim 1 for the diagnosis of multiple sclerosis and wherein from about 0.0001 mg. to about 1.0 mg. is administered subcutaneously, whereby a diagnosis of multiple sclerosis is indicated by a delayed type skin hypersensitivity.

10. The method of claim 1 wherein from about 0.5 mg. to about 5.0 mg. per Kg. of body weight of the recipient mammal, is administered to a mammal afflicted with multiple sclerosis, for the suppression of said multiple sclerosis.

11. A method according to claim 1 wherein said compound is of the formula wherein $n$ is 4.

12. A method according to claim 1 wherein said compound has the formula:

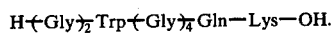

13. A method according to claim 12 wherein each amino acid has the L-configuration.

14. A method according to claim 1 wherein said compound has the formula:

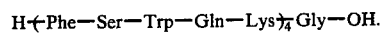

15. A method according to claim 14 wherein each amino acid has the L-configuration.

* * * * *

UNITED STATES PATENT AND TRADEMARK OFFICE
CERTIFICATE OF CORRECTION

PATENT NO. : 4,113,858
DATED : September 12, 1978
INVENTOR(S) : George A. Hashim It is certified that error appears in the above-identified patent and that said Letters Patent are hereby corrected as shown below:

In the Abstract, line 5, delete $R_4$, second instance, in the formula

At Column 2, line 16, - "inducting" should be -- inducing --
At Column 3, line 18, - "kologram" should be -- kilogram --
At Column 5, line 48, - "approximate" should be -- appropriate --
At Column 7, line 6, - "multipl" should be -- multiple --
At Column 14, line 29, - "signals" should be -- signs --

At Column 15, line 58, - "signals" should be -- signs --

At Column 18, line 10, - after the word "followed" delete the word -- by --

At Column 24, line 10 of Claim 1, - delete $R_4$, second instance, in the formula Signed and Sealed this Third Day of April 1979

[SEAL]

Attest:

RUTH C. MASON
Attesting Officer

DONALD W. BANNER
Commissioner of Patents and Trademarks